United States Patent
Gilchrist et al.

(10) Patent No.: US 7,070,722 B1
(45) Date of Patent: Jul. 4, 2006

(54) FOAMABLE FORMULATION AND FOAM

(75) Inventors: Tom Gilchrist, Ayr (GB); Eilidh Trainer, Ayr (GB)

(73) Assignee: Giltech Limited, Ayr (GB)

( * ) Notice: Subject to any disclaimer, the term of this patent is extended or adjusted under 35 U.S.C. 154(b) by 0 days.

(21) Appl. No.: 09/763,983

(22) PCT Filed: Oct. 7, 1999

(86) PCT No.: PCT/GB99/03331

§ 371 (c)(1),
(2), (4) Date: Feb. 28, 2001

(87) PCT Pub. No.: WO00/19979

PCT Pub. Date: Apr. 13, 2000

(30) Foreign Application Priority Data

Oct. 7, 1998 (GB) .................. 9821736.7
Mar. 27, 1999 (GB) .................. 9907065.8

(51) Int. Cl.
*B29D 1/00* (2006.01)
(52) U.S. Cl. .................. 264/50; 524/315; 156/305; 156/306.3
(58) Field of Classification Search ............. 424/401, 424/443, 448, 602, 618, 641, 678, 679, 682; 514/54; 524/272, 315
See application file for complete search history.

(56) References Cited

U.S. PATENT DOCUMENTS

| | | | | |
|---|---|---|---|---|
| 3,962,482 A | * | 6/1976 | Comer et al. ........... | 426/575 |
| 4,086,331 A | | 4/1978 | Neumann ............... | 424/45 |
| 4,201,846 A | * | 5/1980 | Kehr et al. ............. | 521/137 |
| 4,400,391 A | * | 8/1983 | Connick ................ | 424/304 |
| 4,693,728 A | * | 9/1987 | Clare et al. ............ | 8/561 |
| 5,057,606 A | * | 10/1991 | Garbe ................... | 536/54 |
| 5,089,606 A | * | 2/1992 | Cole et al. ............. | 536/54 |
| 5,147,648 A | * | 9/1992 | Bannert ................ | 424/435 |
| 5,641,450 A | * | 6/1997 | Kobayashi et al. ..... | 264/473 |
| 5,641,511 A | * | 6/1997 | Kuhrts ................. | 424/451 |
| 5,851,461 A | * | 12/1998 | Bakis et al. ............ | 264/50 |
| 6,159,512 A | * | 12/2000 | Reyes .................. | 426/102 |
| 6,204,208 B1 | * | 3/2001 | Krzysik et al. ......... | 442/118 |
| 6,280,514 B1 | * | 8/2001 | Lydzinski et al. ...... | 106/122 |

FOREIGN PATENT DOCUMENTS

| | | |
|---|---|---|
| EP | 0 380 254 A2 | 8/1990 |
| GB | 1 503 897 | 3/1978 |
| WO | 94/00512 | 1/1994 |
| WO | 96/17595 | 6/1996 |

* cited by examiner

*Primary Examiner*—Sreeni Padmanabhan
*Assistant Examiner*—Gina Yu
(74) *Attorney, Agent, or Firm*—Drinker Biddle & Reath LLP; Daniel A. Monaco

(57) ABSTRACT

A process for producing a sterile foam for medical or veterinary use is provided. A physiologically acceptable formulation for application to a body as a foam contains a foamable gelling agent. The formulation is foamed and treated with a precipitant which is calcium citrate or a calcium ion. The precipitant is combined with the foamable gelling agent before or during the foaming of the gelling agent. The foam thus obtained is allowed to cure and is then immersed in a bath of the precipitant. The treated foam is dried and sterilized by exposure to gamma-irradiation or ethylene oxide.

11 Claims, No Drawings

FOAMABLE FORMULATION AND FOAM

This application is the U.S. national phase application of PCT International Application No. PCT/GB99/03331 filed Oct. 7, 1999.

The present invention is concerned with a foamable formulation and the foam formed therefrom.

A wide variety of gels, creams, ointments, lotions and other formulations are available for application to a body surface. The exact content of these compositions will vary depending upon the purpose of application. For example, a formulation may be applied to clean a body surface, to promote healing of any wound or injury, to prevent an exposed wound on the body from drying out, to prevent infection, etc. In certain circumstances the composition may include an active ingredient.

In our International Patent Application published Jun. 13, 1996 under No WO-A-96/17595 we describe a foamable formulation which comprises a foamable carrier or gelling agent, for example an alginate gel, and an active ingredient, such as a water soluble glass powder.

The product described in WO-A-96/17595 represented a considerable advance over the use of gel or cream.

We have now found that by including a precipitant for the gelling agent, in a slow-release form within the composition, further improvements with regard to the setting time of the foam and its stability can be achieved. In particular, the added stability enables a pre-foamed pad to be sterilised by irradiation, ethylene oxide, or other conventional means.

Thus, the present invention provides a formulation comprising a foamed gelling agent combined with a slow-release precipitant therefor. The gelling agent may be any agent capable of forming a foam, although preferably the gelling agent is physiologically compatible and non-irritant when maintained in contact with the body surface. The gelling agent may be a gel, for example a sodium alginate gel, carageenan gel, sodium carboxymethylcellulose gel or mixtures thereof.

The precipitant is desirably intimately admixed throughout the whole of the foamed gelling agent, preferably during the foaming process. In certain circumstances however the presence of the precipitant on one surface of the foamed gelling agent may be sufficient to cause stabilisation of the foam. Examples of precipitants include stabilising crosslinking agents which render the gelling agent insoluble. Examples include salts of polyvalent metal ions such as calcium, zinc, or aluminium as well as borates, glyoxal and amino-formaldehyde precondensates. In one embodiment, the polyvalent metal ion may be released from a water-soluble glass which is admixed into the foamable carrier in comminuted form.

The role of the precipitant is to stabilise the foamed gel so that a stable foam is produced. Generally, the stable foam should be produced within a reasonable time period since if the precipitant is too slow-acting, the foam structure will have collapsed prior to stabilisation. However, a very fast acting precipitant may not allow sufficient time for the gel to be foamed. Desirably, the precipitant stabilises the foamed gel over a time period of 1 minute to 120 minutes, preferably within 30 minutes, and most preferably within 15 minutes at ambient temperature. The foam is considered to be "cured" when it can be lifted and carefully handled without collapse. The solubility of the precipitant and hence the setting (cure) time of the foam may be varied by adjusting the pH of the composition, especially where the precipitant is based upon a calcium salt. Generally, the solubility of a calcium salt will be increased by lowering the pH. Typical pH adjusters include organic acids such as acetic, adipic, citric, futnaric, lactic, alginic and tartaric acids. Usually an amount of 0.5 g to 5 g of organic acid per 100 gel is sufficient. The organic acid may be admixed with the precipitant prior to foaming or, more preferably, may be admixed with the gelling agent prior to foaming.

Suitable precipitants include calcium citrate, calcium carbonate, calcium phosphate, calcium hydrogen phosphate ($CaHPO_4$), aluminium chloride, barium carbonate, barium phosphate, barium sulphate, barium chloride and zinc carbonate.

Where the gelling agent comprises an alqinate gel, a carageenan gel or a carboxymethylcellulose gel one preferred precipitant is a calcium salt. Whilst calcium citrate has been used in the examples, other slowly dissolving calcium salts are also suitable.

Where the gelling agent comprises carboxymethylcellulose gel one preferred precipitant is an aluminium salt.

In one embodiment the gelling agent and precipitant are packaged separately and only admixed during the foaming process or subsequent to foaming.

Alternatively, the precipitant may be included in a suspension (e.g. a suspension of calcium citrate and glycerine) which forms a separate layer on top of the gelling agent which remains substantially inert during handling and/or storage. Only once the operator desires to produce the foam, is the precipitant intimately admixed with the gelling agent (for example by shaking the container) and then promptly foamed. Using the precipitant in suspension form has the benefit that the suspension is easier to dispense from a pressurised container than a powder and also provides for more accurate dosing of unit precipitant per unit gelling agent.

Optionally, the formulation may comprise other additives such as decompactants which promote the desired foam structure or other foaming agents, plasticisers, humectants, preservatives, additives, sequestering agents or active ingredients such as antimicrobial agents, growth factors, hormones, living cells, etc.

The foam may be applied directly to the body area and allowed to produce a stable foam protective cover, for example over a wound. With the addition of the precipitants the cure of the foam is significantly reduced, rendering the product more user friendly.

Alternatively, the foam can be produced onto a mould or other surface area, allowed to cure (for example by air drying or oven drying) and then applied to the body surface as a dressing. A foam sheet of this type is a preferred embodiment of the invention since it exhibits sufficient stability for easy handling whilst retaining a moist surface to promote wound healing. Optionally, the foam may be applied about a substrate which are then integrated into the foam pad produced.

As an example, the foam may be used to treat dermatological conditions (including psoriasis, atopic and allergic eczema). It may be convenient in this embodiment for the foam to deliver an active ingredient normally used to alleviate such conditions, for example a steroid such as hydrocortisone.

In another embodiment the foam may be used to treat burns or scalds, including sunburn.

In another embodiment the foam may be applied cosmetically, and for example may include skin moisturising agents, nutritional agents and growth factors suitable to promote skin regeneration. A foam intended for cosmetic use may include colorants or pigments so that the foam may be applied to the skin as a cosmetic or to disguise any blemishes in the skin.

The foam may be used prophylactically. In particular a foam containing a UV blocking agent may be applied to exposed areas of the skin to protect it from the effects of the sun.

The formulation of the invention is applied to the body site of interest in the form of a foam and it is therefore essential that the composition undergoes a foaming process before application to the body. In the foaming process gas is forced into or is formed within the formulation to entrap small bubbles of gas therein, thereby forming the foam. Any suitably gas or gas producing system can be used to produce the foam. Mention may be made of butane and nitrous oxide, but other gases like air, nitrogen, hydrof luorocarbons such as HFC134a or 227, hydrocarbons like propane, isopropane or a mixture thereof, are also suitable. Conveniently the foam may be produced by conventional means such as by using aerosol technology.

The formulation according to the present invention may be stored in any convenient container until required. Generally, the container will be designed to preserve the sterile nature of the formulation. Conveniently the container will be provided with means to foam the composition when required. Details are given in WO-A-96/17595. A two can packaging-and dispensing system, as described in our co-pending UK Patent Application No 9823029.5 (a copy of which is filed herewith), may be used to dispense the foam according to the present invention.

Generally, the foam will be produced from sterile ingredients.

Prior to the foaming process, the foamable carrier is preferably in the form of a gel. The gel may be sterilised and this is generally desirable where the foam is intended for medical use. Usually, sterilisation will take place by autoclaving the formulation, since this is currently the most economic means of achieving sterilisation. Autoclaving at temperatures of from 100° C. to 125° C. for under ½ hour is normally sufficient. Generally, the autoclaving process should be as mild as possible, whilst being sufficient to sterilise the formulation. For example, autoclaving at temperatures of about 121° C. for 15–20 minutes is acceptable. The autoclaved formulation may then be foamed when cool. It is also possible, however, to sterilise the formulation by other means, for example by γB-irradiation or e-beam irradiation. It has been found that autoclaving the gel may cause the MW of the foamable carrier to be slightly reduced. Consequently it may be desirable to select a foamable carrier having a higher MW than that ultimately required.

The foam forms an air-tight cover around any wound or injury to which it is applied, and this prevents that area from drying out and may also combat infection. The advantages of applying a topical product in the form of a foam include:
1. Easy rapid application,
2. Conforms to surface irregularities,
3. Insulates the wound,
4. Cools the tissues,
5. Offers antibacterial action to prevent infection,
6. Biocompatibility with tissue.,
7. Suitable for use as a vehicle for the administration of pharmaceutical agents, and/or
8. Maintains a moist environment.

Generally, the formulation of the present invention will be applied directly to the body site of interest in the form of a foam, the foam being produced from any suitable device (such as an aerosol) immediately before application. It is, however, possible for a quantity of the foamed formulation to be produced and then applied onto the body site by any suitable means, for example by hand or by spatula. This method may be required for wounds having a narrow opening.

As stated above, the foam may also be produced on a suitable surface and then allowed to dry to produce a stable foam sheet which can be handled as described above without deterioration. Generally, the production of the sheet will take place under sterile conditions or may be sterilised after production. In the prior described foam product of WO-A-96/17595, it was not possible to provide a foamed pad product and then sterilise the pad by conventional means such as γ-irradiation, since it was found that the foam structure deteriorated during sterilisation. With the inclusion of the precipitant however, sterilisation of the pad is possible both by γ-irradiation, ethylene oxide sterilization or other conventional means. This represents a very considerable advantage over the prior art product.

The foam sheet is generally produced by foaming the foamable carrier in the presence of the precipitant and allowing the foam to cure, usually by simply exposing the foam to the atmosphere to air dry at ambient temperature. Optionally the foam may be dried at elevated temperatures,. for example may be oven dried. Desirably, the cure time of the foam is 40 minutes or less at ambient temperature and preferably the foam cures within 15 minutes, for example within 10 minutes.

Where the foam sheet is to be sterilised, it is advantageous to pre-treat the sheet prior to sterilisation in order to further stabilise the sheet. The difficulty with sterilising any foam of the type described is that the foam structure tends to deteriorate and collapse during the sterilisation process. The pre-treatment of the sheet preferably involves impregnating the sheet with further precipitant. Conveniently, this may entail immersing the sheet in a bath of the precipitant or of a solution of the precipitant. For example, the sheet may be immersed in a bath of calcium chloride or calcium citrate. To ensure that the precipitant penetrates into the centre of the foam sheet, the sheet may be gently squeezed whilst immersed in the bath. Generally, immersion of the sheet for a short period of time, such as 2 to 3 minutes, is sufficient. The sheet may then be removed from the bath of precipitant, washed in a mixture of de-ionised water and glycerine to enhance moisture content and then dried. The stabilised foam sheet may then be sterilised by gamma radiation or through use of ethylene oxide.

The ratio of de-ionised water : glycerine in the wash stage is preferably 19:1 by volume.

The treated foam sheet is desirably oven dried at relatively low temperatures, for example 100° C. or less, preferably approximately 35° C.

We consider that any material known for its use as a free radical scavenger and/or as a radioprotectant may likewise exhibit a protective effect on the foam structure during sterilisation.

Optionally the manufacture of a prefoamed product may envisage a continuous foaming process. The sheet may be divided into a convenient size and may be packaged. Optionally the foam sheet may be produced on contoured surface so that it is moulded to a predetermined shape.

Examples of suitable foamable gelling agents for use in the composition of the present invention include (but are not limited to) alginate and derivatives thereof, carboxymethyl-cellulose and derivatives thereof, collagen, polysaccharides (including, for example, dextran, dextran derivatives, pectin, starch, modified starches such as starches having additional carboxyl and/or carboxamide groups and/or having hydrophillic side-chains, cellulose and derivatives thereof), agar and derivatives thereof (such as agar stabilised with polyacrylamide), carageenan, polyethylene oxides, glycol methacrylates, gelatin, gums such as xanthum, guar, karaya, gellan, arabic, tragacanth and locust bean gum. Also suitable are the salts of the aforementioned carriers, for example, sodium alginate. Mixtures of any of the aforementioned gelling agents may also be used, as required.

Preferred foamable gelling agents include alginate, carageenan, carboxymethylcellulose, the derivatives and salts thereof and mixtures of any of these. Alginate (the derivatives or salts thereof, such as sodium and calcium alginate) are especially preferred. Foamable gelling agents having a molecular weight of from 10,000 to 200,000 kDa are preferred, especially over 100,000 kDa, for example 150,000 to 200,000 kDa, may be used.

The formulation may further comprise a foaming agent, which promotes the formation of the foam. Any agent having a surfactant character may be used. The surfactants may be cationic, non-ionic or anionic. Examples of suitable foaming agents include cetrimide, lecithin, soaps, silicones and the like. Commercially available surfactants such as Tween™ are also suitable. Cetrimide. (which additionally has an anti-bacterial activity) is especially preferred.

The formulation of the present invention (and thus the foam) may be used to deliver pharmaceutically active agents, in particular to deliver such agents in a controlled release manner. Mention may be made of:

Antiseptics, Antibacterials and Antifungal agents, such as Chlorhexidine, acetic acid, polynoxylin, povidone iodine, mercurochrome phenoxyethanol, acridene, dyes eg brilliant green and undecanoic acid, metronidazole, benzaclonium chloride;

Nutritional agents, such as vitamins and proteins;

Growth factors and healing agents, including Ketanserin a serotonomic blocking agent;

Living Cells;

Enzymes include streptokinase and streptodormase;

Elements—zinc, selenium, cerium, manganese, cobalt, boron, arsenic, chromium gold, gallium;

Charcoal;

Desloughing and Debriding agents such as hypochlorite and hydrogen peroxide;

Astringents including potassium permanganate;

Antibiotics exemplified by neomycin and framycetin sulphate, sulfamylon, fusidic acid, mupirocin, bacitracin, gramicidin.

In addition the formulation of the present invention may further comprise other conventional additives such as plasticisers and humectants (such as glycerol, propane-1,2-diol, polypropylene glycol and other polyhydric alcohols), free radical scavengers to stabilise against the effects of sterilisation by irradiation, viscosity-adjusting agents, dyes and colorants, and the like.

Several experiments including comparatives tests have been made in order to demonstrate some of the advantages of the new compositions of the invention. Of course the embodiments described hereinbelow are submitted in order to better describe the invention and not to limit its scope.

EXAMPLE 1

PROCEDURE FOR MANUFACTURE OF UNIT BATCH (100 g) of ALGINATE GEL

Typically the alginate gels are made according to the following process:

1. De-ionised (DI) water is measured and poured into mixing vessel 1.

2. Desired amounts of suitable alginate (for example Keltone or Manucol) and glycerine are weighed using a calibrated balance, reading to 2 decimal places.

3. Alginate and glycerine are mixed together in a beaker until no lumps remain.

4. The whole alginate/glycerine mix is added very slowly to the water.

5. Once all the alginate/glycerine has been added to the water, the mixture is stirred until a smooth gel has formed.

Several different alginate gels have been made according the above process. They differ and are referred to by the amount of alginate (for example Kel-tone) used. For example the alginate gel code 6½ has the following composition:

| GEL CODE | 6½ |
|---|---|
| DI Water | 80 ml |
| Glycerine | 25.22 g |
| Keltone | 6.5 g |
| Unit Batch Wt | 111.72 g |

The above composition can be varied to include other weights of alginate, which would be reflected in the gel code number. For example a composition having 8 g alginate (plus 80 ml DI water and 25.22 g glycerine) would be designated gel code 8. Analogous gel codes are used when other gel formers (eg carageenan or CMC) are substituted for the alginate in the above composition.

In one embodiment, the gelling agent may be present in the form of a suspension, for example a suspension in glycerine. To avoid diluting the gelling agent, the gelling agent suspension may be made up with less glycerine such that the total quantity of glycerine present in the gelling agent mixture and in the precipitant suspension adds up to the required amount. For example, the glycerine in the gelling agent mixture and precipitant suspension may be varied as follows:

| Glycerine per 80 ml DI water and 6 g alginate (g) | Glycerine in precipitant suspension (g) |
|---|---|
| 25.22 | 0 |
| 23.0 | 2.22 |
| 20.0 | 5.22 |
| 18.22 | 7.0 |
| 15.0 | 10.22 |

The above is illustrated with respect to a gel code 6 composition, but the division of glycerine may be made for other gel code compositions, and is also not limited to the specific volumes illustrated above.

PROCEDURE FOR FOAM PRODUCTION

The propellant used to produce the foam can be compressed gases such as air, nitrogen, nitrous oxide or air, hydrofluorocarbons such HFC134a or 227 or hydrocarbons including propane, isopropane, n-butane, isobutane and 2-methylbutane.

Propellant vapour pressure can range from 0 to 110 PSIG at 70° C. although, the preferred range is 20 to 70 PSIG. Values within this range can be achieved for example by blending the three hydrocarbons propane, isobutane and butane. Calor Aerosol Propellants (CAP) sold by Calor Gas Ltd Slough may be used as propellant gas, when a blend of propane, isobutane and butane is used the proportions can be as follows:

| Grade | Propane % | Isobutane % | n Butane % |
|---|---|---|---|
| CAP 30 | 11 | 29 | 60 |
| CAP 40 | 22 | 24 | 54 |
| CAP 70 | 55 | 15 | 30 |

A foam according to the invention can advantageously be produced following the following process:

1. 100 g of a gel according to the invention is poured to an aerosol canister.
2. 2.5 g of calcium citrate (food grade) is added to the canister.
3. A valve is crimped onto the canister.
4. Air is purged from the canister.
5. 4.5 g of propellant gas is added into the canister (65:35 CAP 40 : Isopentane propellant) and an actuator is positioned on the valve.
6. The canister is shaken vigorously for 20–30 seconds.
7. The canister is inverted and the foam dispensed.

EXAMPLE 2

Using a range of water-based gel formulations detailed below tests were done to improve the "setting" time and stability of the gel and its foam.

Preferred alginate compositions have an amount of alginate ranging from 5–9 g in the composition set out in Example 1. Preferred alginates are Keltone HV and Manucol DMF.

Experiment 1. Gel Code 6½ Alginate gel and foam mixed with calcium citrate compared to Gel Code 6½ alginate gel alone Foamed gel with calcium citrate 2.5 g calcium citrate was added to 100 g of gel and the foamed gel was spread out onto plastic sheeting. The resultant foam pad was liftable in 15 minutes.

Foamed gel without calcium citrate

The above experiment was reproduced by foaming the gel on its own as described above. The "setting" time of the foam was 10 hours.

The experiments were repeated using 100 g unfoamed gel with and without calcium citrate. Similar setting times to those observed for the foamed gels were obtained (15 minutes and 10 hours respectively) before the gel pads were liftable.

Conclusion: Calcium citrate speeds up and controls the setting time of the gel and the foam.

Experiment 2. Gel Code 4 Carageenan gel mixed with calcium citrate compared to gel code 4 gel alone Foamed gel with calcium citrate 3 g of calcium citrate was mixed with 100 g gel and the foamed mix was spread out onto plastic sheeting. The resultant foam pad was liftable in 120 mins.

Foamed gel without calcium citrate

The above experiment was repeated by foaming gel on its own as described above. The "setting" time of the foam was 10 hours.

The experiments were repeated using 100 g unfoamed gel with and without calcium citrate. Similar setting times to those observed for the foamed gels were obtained (120 minutes and 10 hours respectively) before the gel pads were liftable.

Experiment 3. Gel Code 4½ Carageenan gel and gel code 6½ alginate gel mixed with calcium citrate compared to gel code 4½ carageenan gel and gel code 6½ alginate gel alone Foamed gel with calcium citrate 2.5 g of calcium citrate was mixed with (50 g alginate and 50 g carageenan) gel and the foamed mix was spread out onto plastic sheeting. The resultant foam pad was liftable in 15 mins.

Foamed gel without calcium citrate

The above experiment was repeated by foaming the mixed gel on its own. The "setting" time of the foam pad was 10 hours.

The experiments were repeated using 100 g unfoamed gel with and without calcium citrate. Similar setting times to these observed for the foamed gels were obtained (120 minutes and 10 hours respectively) before the gel pads were liftable.

Experiment 4. Gel Code 6½ Alginate gel mixed with calcium citrate and added bentone IPM gel 2.5 g calcium citrate was added to 100 g of gel with 1 g bentone IPM gel, admixed in an aerosol canister and dispensed therefrom as a foam onto a plastic surface. The resultant foam pad was liftable in 12 minutes. Bentone IPM gel is an admixture of isopropyl myristate, sterealkonium hectorite and propylene carbonate.

Conclusion: Calcium citrate and bentone gel control the setting time of the foam. Bentone gel also acts as a reological agent and assists in the smoothness of delivery from the can.

Experiment 5. Gel Code 6½ Alginate gel mixed with calcium citrate and added cetrimide 2.5 g calcium citrate was added to 100 g of alginate gel with 1 g cetrimide in an aerosol canister and foamed onto a plastic surface. The resultant foam pad was liftable in 15 minutes.

Conclusion: Calcium citrate speeds up the setting time of the foam. Cetrimide increases the cell structure of the product.

Experiment 6. Gel Code 6½ Alginate gel mixed with calcium citrate and added Tween 20

2.5 g Calcium citrate was added to 100 g of alginate gel with 1 g Tween 20 and foamed onto a plastic surface. The resultant foam pad was liftable in 12 minutes.

Conclusion: Calcium citrate speeds up the setting time of the gel. The additive Tween 20 gave a much smoother delivery and an airier foam. Tween 80, 60 and 40 were also tried and all assisted in the delivery and product cell structure.

Experiment 7. Gel Code 4 Carboxmethyl cellulose and gel code 6½ alginate gel mixed with calcium citrate compared to the gel alone 2.5 g calcium citrate was added to (50 g CMC & 50 g alginate gel) and then the mixture was foamed onto a plastic surface. The resultant foam pad was liftable in 25 minutes. The gel foamed on its own was liftable overnight (approx. 10 hours).

Experiment 8. Gel Code 4 Carboxmethyl cellulose gel mixed with aluminium chloride compared with the gel alone 2 g aluminium chloride was mixed with 100 g CMC gel. The gel was spread onto a plastic surface. The resultant gel was liftable instantly. The gel alone was liftable overnight. (approx. 10 hours).

Experiment 9. Gel Code 6 Alginate gel mixed with citric acid compared to gel code 6 alginate gel alone 2.5 g of citric acid was mixed with 100 g alginate gel and the mix was spread out onto plastic sheeting. The resultant gel pad was liftable in 120 mins. 100 g of the gel alone was spread onto plastic sheeting and the resultant pad was only liftable overnight (approx. 10 hours).

Experiment 10. Gel Code 6½ Alginate gel was mixed with the following powders on a 100 g gel: 2.5 g powder basis

| Powder | Results as a gel | Results as a foam |
| --- | --- | --- |
| Calcium Chloride | Gel pad was formed instantly | Fast setting foam |
| Calcium Sulphate | Gel pad formed reasonably quickly | Foam set reasonably quickly |
| Aluminium Chloride | Gel pad formed instantly | Fast setting foam |
| Calcium Metaborate | Gel pad formed instantly | Fast setting foam |

Experiment 11. Setting performances of a foam of a gel code 6½ alginate gel as a function of the amounts of calcium citrate.

| Batch No | Amount of calcium citrate per 100 g gel | Result |
| --- | --- | --- |
| DM02 210798 | 4 g | Not dispensed - set in can |
| DM03 210798 | 3 g | Very difficult to dispense. 9½ minutes to set. |
| DM04 210798 | 2.5 g | Easier to dispense than above. 18½ minutes to set |
| DM05 210798 | 2.25 g | Taking longer to set. 20 minutes. |
| DM02 200798 | 2 g | Setting time - 40 minutes |

Experiment 12. Gel Code 6½ alginate gel with calcium citrate and isopentane.

100 g gel code 6½ alginate gel was admixed with varying amounts of calcium citrate (2 to 4 g) added to isopentane and mixed thoroughly before being spread onto a glass sheet. The isopentane vaporises at ambient temperatures and boils off through the gel leaving a foam pad of similar consistency to those produced by dispersion from an aerosol can. After half-an-hour the foam pads were liftable.

EXAMPLE 3

A. Gel code 5 alginate gel mixed with calcium citrate

The gel was prepared by mixing together alginate (5 g Keltone HV), 20 g glycerine and 80 ml de-ionised water.

5.22 g glycerine was then added to 2.5 g calcium citrate and a suspension of precipitant was created. The resultant gel and the suspension of precipitant were added to an aerosol can and a valve fitted. The can was purged of air, filled with 4.5 g CAP 40 butane,, shaken and dispensed. The foam produced was well mixed and set in 15 minutes.

B. Gel code 5 alginate gel mixed with calcium citrate

Experiment A was repeated using the same weight of Manucol LKX (5 g) instead of Keltone HV. The resultant foam set within 12 minutes.

C. Gel code 5 alginate gel mixed with calcium citrate

The gel was prepared by mixing together alginate (5 g Keltone HV), 20 g glycerine and 80 ml de-ionised water.

5.22 g glycerine was then added to 2.5 g calcium citrate and a suspension of precipitant was created. The resultant gel was added to the bottom can of the two can packaging system (see our co-pending UK Patent Application No 9823029.5) and the suspension or precipitant was added to the top can. The cans were prepared in the usual way. The two can packaging system was activated and the foam was dispensed. The foam produced was well mixed and set in 15 minutes.

D. Gel code 5 alginate gel mixed with calcium citrate

Experiment C was repeated using the same weight of Manucol LKX instead of Keltone HV. The resultant foam set within 12 minutes.

The set foam from A, B, C and D were then further processed by first immersing the foam in a solution of 2.5% calcium chloride solution for 2 minutes, rinsing in de-ionised water and then finally rinsing in a 1% glycerine solution. The foam pads were then dried in the oven at 35° C. and packaged in sterilisable pouches.

The resultant sterilised pads were compared with can reference 2 below (see Example 4). The foams produced in the two can system had a more even pore size throughout compared to those made in a one can system. Comparing the suspension with the powder/gel mix showed no difference in the structure of the final product.

EXAMPLE 4

A 1 litre batch of gel code 5 alginate gel was manufactured. Nine bottom cans of a two can packaging system as described in our co-pending UK Patent Application No 9823029.5 were filled with 100 g gel in each. Nine top cans were made up with varying powders as detailed below. The cans were prepared in their usual way. The two can packaging system was activated and the foam was dispensed.

Once cured the foams were processed by varying a) the concentration of the calcium: chloride immersion solution and b) the final wash concentration of the glycerine solution. All samples were halved and then oven dried at 40° C. The first half sample was removed after 8 hours and the second half after 16 hours. Once the foam pads had been processed they were packaged in EtO sterilisable airtight packaging as soon as they came out of the oven. The samples were sent for EtO sterilisation and examined on their return.

| Can Ref | Top Can Component | Ca Chloride Conc. | Glycerine Sol Conc. | Drying Time | Description of Alginate Pad After EtO Sterilisation |
|---|---|---|---|---|---|
| 1 | 2.5 g Ca Citrate | 1% | 1% | 8 hrs | Flexible, soft & sponge-like |
|   |   |   |   | 16 hrs | Flexible, soft & sponge-like, |
| 2 | 2.5 g Ca Citrate | 2.5% | 1% | 8 hrs | Moist, flexible & sponge-like |
|   |   |   |   | 16 hrs | Flexible, soft & sponge-like |
| 3 | 2.5 g Ca Citrate | 5% | 1% | 8 hrs | Dry pad with limited flexibility |
|   |   |   |   | 16 hrs | Dry pad with limited flexibility |
| 4 | 2.5 g Ca Citrate | 2.5% | 2% | 8 hrs | Moist, flexible, soft & sponge-like |
|   |   |   |   | 16 hrs | Moist, flexible, soft & sponge-like |
| 5 | 2.5 g Ca Citrate | 2.5% | 2.5% | 8 hrs | Moist, flexible, sponge-like pad |
|   |   |   |   | 16 hrs | Moist, flexible, sponge-like pad |
| 6 | 2.5 g Ca Citrate | 2.5% | 5% | 8 hrs | Moist, flexible, soft & sponge-like |
|   |   |   |   | 16 hrs | Moist, flexible, soft & sponge-like |
| 7 | 2 g Ca Citrate 2 g Activated Charcoal | 2.5% | 5% | 8 hrs | Moist, flexible, soft & sponge-like |
|   |   |   |   | 16 hrs | Moist, flexible, soft & sponge-like |
| 8 | 2 g Ca Citrate 2 g Povidone Iodine | 2.5% | 5% | 8 hrs | Moist, flexible, soft & sponge-like |
|   |   |   |   | 16 hrs | Moist, flexible, soft & sponge-like |

EXAMPLE 5

Experiment A

A 600 g batch of gel code 5 was made up using Manucol DMF as the gelling agent. This batch was split into six equal parts and inserted into the bottom can of a dual can aerosol system. The top cans were made up containing 1.5 g calcium citrate and varying amounts of alginic acid (∕1;2 g increments from 0 to 2∕1;2 g). Once preparation was complete the cans were foamed out simultaneously and the setting time for each foam was recorded.

| Can Number | Gel Weight | Calcium Citrate Weight | Alginic Acid Weight | Setting Time |
|---|---|---|---|---|
| 1 | 100 g | 1.5 g | 0 g | 20 mins |
| 2 | 100 g | 1.5 g | 0.5 g | 16 mins |
| 3 | 100 g | 1.5 g | 1.0 g | 14 mins |
| 4 | 100 g | 1.5 g | 1.5 g | 10 mins |
| 5 | 100 g | 1.5 g | 2.0 g | 9 mins |
| 6 | 100 g | 1.5 g | 2.5 g | 8 mins |

Experiment B

Three 100 g batches of gel code 5 was made up using Manucol DMF as the gelling agent with alginic acid incorporated (0 g, 1 g and 2 g added). Each batch was filled into bottom cans and top cans were made up containing 1.5 g calcium citrate. Once preparation complete the cans were foamed out simultaneously and the setting times for each can recorded.

| Can Number | Gel Weight | Calcium Citrate Weight | Alginic Acid Weight | Setting Time |
|---|---|---|---|---|
| 7 | 100 g | 1.5 g | 1 g | 8 mins |
| 8 | 100 g | 1.5 g | 2 g | 6 mins |
| 9 | 100 g | 1.5 g | 0 g | 20 mins |

The invention claimed is:
1. A process of producing a sterile foam for medical or veterinary use, said process comprising the following steps:
   a) forming a physiologically acceptable foam for application to a body, said foam comprising a foamable gelling agent, and wherein said gelling agent is treated with a first precipitant which is calcium citrate, calcium-releasing water-soluble glass, or a combination thereof, and wherein said first precipitant is combined with said gelling agent before or during the foaming of the gelling agent and stabilises the gelling agent;
   b) allowing the foam thus obtained to cure;
   c) immersing the cured foam in a bath of a second precipitant which is calcium citrate, calcium-releasing water-soluble glass, or a combination thereof, to form a treated foam;
   d) drying the treated foam; and
   e) sterilising said dried treated foam by exposure to gamma-irradiation or ethylene oxide.

2. A process as claimed in claim 1, wherein said precipitant is packaged separately to said foamable gelling agent prior to forming the physiologically acceptable foam of step a).

3. A process as claimed in claim 1, wherein said gelling agent is alginate, collagen, a polysaccharide, agar, a polyethylene oxide, a glycol methacrylate, carageenan gel, gelatin, a gum, or salt of any of these, or mixtures thereof.

4. A process as claimed in claim 3 wherein said gelling agent is alginate, salts thereof, or mixtures thereof.

5. A process as claimed in claim 1, wherein said gelling agent has a molecular weight of from 10,000 to 200,000 kDa.

6. A process as claimed in claim 1, wherein said sterile foam further contains a foaming agent.

7. A process as claimed in claim 6, wherein said foaming agent is cetrimide, lecithin, a soap, silicone, or a surfactant.

8. The process of claim 1, wherein said foamable gelling agent further comprises an organic acid in an amount of 0.5 g to 5.0 g per 100 g of gelling agent.

9. The process of claim 1, wherein said treated foam is washed in a de-ionised water/glycerine mixture prior to drying.

10. The process of claim 1 wherein the treated foam is oven dried at temperatures below 100° C.

11. The process of claim 1, wherein said treated foam is washed.

* * * * *